United States Patent
Urisu et al.

(10) Patent No.: US 10,114,005 B2
(45) Date of Patent: Oct. 30, 2018

(54) PLANAR PATCH CLAMP DEVICE, ELECTRODES FOR SAID DEVICE AND CELL ION CHANNEL CURRENT MEASUREMENT METHOD

(71) Applicant: Japan Science and Technology Agency, Kawaguchi-shi, Saitama (JP)

(72) Inventors: Tsuneo Urisu, Okazaki (JP); Zhi-hong Wang, Nagoya (JP); Hidetaka Uno, Toyota (JP); Senthil Kumar Obuliraj, Nagoya (JP); Yasutaka Nagaoka, Nagoya (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 670 days.

(21) Appl. No.: 14/366,708

(22) PCT Filed: Dec. 5, 2012

(86) PCT No.: PCT/JP2012/081556
§ 371 (c)(1),
(2) Date: Jun. 19, 2014

(87) PCT Pub. No.: WO2013/094418
PCT Pub. Date: Jun. 27, 2013

(65) Prior Publication Data
US 2014/0339102 A1    Nov. 20, 2014

(30) Foreign Application Priority Data

Dec. 20, 2011 (JP) ................................. 2011-278445
Aug. 20, 2012 (JP) ................................. 2012-181786

(51) Int. Cl.
*G01N 33/487* (2006.01)
*G01N 27/416* (2006.01)

(52) U.S. Cl.
CPC ..... *G01N 33/48728* (2013.01); *G01N 27/416* (2013.01)

(58) Field of Classification Search
CPC ........................ G01N 33/48728; G01N 27/416
See application file for complete search history.

(56) References Cited

U.S. PATENT DOCUMENTS

2002/0063067 A1 * 5/2002 Bech ................ G01N 33/48728
                                                      205/775
2006/0251709 A1 * 11/2006 Ide ........................ A61K 9/127
                                                      424/450

(Continued)

FOREIGN PATENT DOCUMENTS

GB      2 060 896 A    5/1981
JP    2004-510980 A    4/2004

(Continued)

OTHER PUBLICATIONS

Woonik Park, "Fabrication and performance of Ag/AgCl reference electrode and its application to pH sensor", Department of Materials Science and Engineering Korea Advanced Institute of Science and Technology, Advisor: Professor Chong-Ook Park, Master's thesis (Dec. 20, 2005).

(Continued)

*Primary Examiner* — Sally A Merkling (57) ABSTRACT

An object of the present invention is that variations in an applied membrane potential in the planar patch clamp device are suppressed to reduce a noise current, thereby enabling accurate measurement of an ion channel current.
Disclosed is a planar patch clamp device including: an electrically insulative substrate provided with one or more fine through holes; a liquid reservoir that holds a conductive liquid provided on both surface sides of the through hole; and energizable electrode sections provided in the liquid reservoir; these electrode sections including: (a) an electrode (Continued)

vessel, at least part of which is made of an inorganic porous material, (b) an electrode in which a chloride NmCl layer is formed on the surface of a noble metal Nm, and (c) an electrode solution containing NmCl and an alkali metal chloride being dissolved therein at a saturated concentration.

13 Claims, 5 Drawing Sheets

(56) References Cited

U.S. PATENT DOCUMENTS

2008/0286750 A1    11/2008  Xu et al.
2009/0281410 A1*  11/2009  Ushio .............. G01N 33/48728
                                                                   600/395

FOREIGN PATENT DOCUMENTS

| JP | 2008-039624 A | 2/2008 |
| JP | 2009-195107 A | 9/2009 |
| JP | 2009-204407 A | 9/2009 |
| WO | 2002/029402 A2 | 4/2002 |

OTHER PUBLICATIONS

European Patent Office, "Extended European Search Report," issued in European Patent Application No. 12 859 984.2, which is a European counterpart of U.S. Appl. No. 14/366,708, dated Aug. 3, 2015, 8 pages.

* cited by examiner

PLANAR PATCH CLAMP DEVICE, ELECTRODES FOR SAID DEVICE AND CELL ION CHANNEL CURRENT MEASUREMENT METHOD

CROSS REFERENCE TO RELATED APPLICATIONS

This patent application is a U.S. national stage application under 35 U.S.C. § 371 of International Patent Application No. PCT/JP2012/081556 filed on Dec. 5, 2012, which claims the benefit of foreign priority to Japanese Patent Application No. JP 2011-278445 filed on Dec. 20, 2011, and to Japanese Patent Application No. JP 2012-181786 filed on Aug. 20, 2012, the disclosures of all of which are hereby incorporated by reference in their entireties. The International Application was published in Japanese on Jun. 27, 2013, as International Publication No. WO 2013/094418 A1 under PCT Article 21(2).

TECHNICAL FIELD

The present invention relates to a planar patch clamp device, an electrode section for the device, and a cell ion channel current measurement method.

More specifically, the present invention relates to a planar patch clamp device that is a planar substrate type enabling multipoint measurement, and has the cell culture function, and also enables effective suppression of a noise current and stable positioning of cells at ion channel current measurement; an electrode section for a planar patch clamp device to be incorporated into this device; and a cell ion channel current measurement method using this planar patch clamp device.

BACKGROUND ART

Various membrane proteins are disposed on the surface of cells constituting an organism. Channels, which are openings of membrane proteins, are opened or closed by binding of chemicals (signaling substances such as ligands) to specific sites on the cell surface or electrical or photic stimulation (gate trigger), resulting in regulation of the transport of ions or chemicals between the outside and inside of cell membrane. This regulation is performed by ion channels, which are important membrane proteins involved in signal transduction in biological systems. In measurement of their function or development of drugs related to the function, measurement of electrical changes in channel proteins, i.e., ion channel current, is required.

To meet this demand, technologies such as pipette patch clamp and planar patch clamp have been developed. Pipette patch clamp has a drawback that it cannot be applied to high-throughput screening by multipoint measurement. On the other hand, planar patch clamp constitutes a plurality of patch clamp devices on a solid substrate such as silicon tip, thereby enabling multipoint measurement. Each patch clamp device includes fine through holes to measure an ion channel current at each cell placement site.

For example, the following Patent Literature 1 mentions a planar patch clamp electrode array including a plurality of electrodes in order to perform patch clamp recording with a plurality of patch clamp cells. The following Patent Literature 2 discloses a planar patch clamp device which is disposed with electrodes disposed on the upper and lower surfaces of a silicon substrate, and a through hole that conductively communicate between the two electrodes, thus measuring electrical changes in a cell disposed on the through hole.

PRIOR ART REFERENCE

Patent Literature

[Patent Literature 1]
Kohyo (National Publication of Translated Version) No. 2003-511668
[Patent Literature 2]
Kohyo (National Publication of Translated Version) No. 2005-536751
[Patent Literature 3]
Kokai (Japanese Unexamined Patent Application Publication) No. 2009-204407

Non Patent Literature

[Non Patent Literature 1]
Tsuneo Urisu et al., Analytical and Bioanalytical Chemistry, 391 (2008) 2703-2709

SUMMARY OF INVENTION

Technical Problem

Since conventional planar patch clamp devices have no cell culture function, there was a problem that they could not be applied to cells that require culture such as nerve cells. In other words, since the life span of a cell to be measured is as short as 1 hour or 30 minute or less under non-culture conditions, the application is limited to drug discovery screening, etc. and it was difficult to apply the devices to cell function analysis in which pipette patch clamp has been utilized. Furthermore, it was difficult to successfully convey a cell to the site of fine through hole disposed on a substrate and trap it.

Urisu and Uno proposed a planar patch clamp device that solves the above problems in the above Patent Literature 3 (Application Number: Japanese Patent Application No. 2008-046145) and Non Patent Literature 1. The constitution of this device is characterized by an extracellular matrix-forming substance having cell fixing capability (e.g., collagen, fibronectin) attached on the circumference of the opening for cell fixing of a fine through hole disposed on a substrate; a liquid reservoir, which is capable of being energized, disposed on the surface on both sides of the through hole on the substrate; and this liquid reservoir filled with a conductive liquid (e.g., cell culture medium). According to this planar patch clamp device, a cell can easily be trapped to the site of fine through hole by the extracellular matrix-forming substance, and furthermore, ion channel activity can be measured for a sufficient time under cell culture conditions.

However, further studies revealed that the planar patch clamp device according to the above proposal has the following problems 1) and 2).

1) Since an extracellular matrix-forming substance is attached on the circumference of a fine through hole on which an ion channel current is measured, there is a slight gap between the cell membrane of a trapped cell and the substrate surface of the circumference of the fine through hole, resulting in decrease in so-called seal resistance. The current in the gap is added as a leak current to the ion channel current, and variations in this current contribute as noise. Therefore, under the condition of decreased seal resistance, a noise current is increased for slight variations in an applied membrane potential and accurate measurement of an ion channel current becomes difficult.

To resolve this problem, if simply the use of an extracellular matrix-forming substance is abandoned, the advantage that cells can easily be trapped to the site of fine through hole is also lost. On the other hand, as measures against the above noise current, it is effective to increase a seal resistance and to suppress variations in an applied membrane potential on electrode side. Also when originally a seal resistance is not low, measures against a noise current based on variations in an applied membrane potential is effective for more accurate measurement of an ion channel current.

2) A cell trapped at the site of fine through hole often moves to a site outside the fine through hole under cell culture conditions. Due to such cell movement, an ion channel current cannot be measured.

Thus, a first object to be achieved of the present invention is that variations in an applied membrane potential in the planar patch clamp device are suppressed to reduce a noise current, thereby enabling accurate measurement of an ion channel current.

A second object to be achieved of the present invention is to develop a technology to fix a cultured cell trapped at the site of fine through hole so that the cell remains at the site.

Solution to Problem (Constitution of First Invention)

The constitution of a first present invention to achieve the above objects resides in a planar patch clamp device including: (1) an electrically insulative substrate provided with one or more fine through holes, each having an inner diameter through which a cell cannot pass but a liquid can pass, the fine through holes communicating between surfaces on both sides of the electrically insulative substrate; (2) a liquid reservoir that holds a conductive liquid, and an electrode section disposed energizably for a conductive liquid in the liquid reservoir, provided on a first surface side and a second surface side of the through hole; (3) the liquid reservoir on the first surface side serving as a liquid reservoir for cell placement; and (4) the following constituents (a) to (c) included in electrode sections on the first surface side and second surface side:

(a) an electrode vessel, at least part of which is made of an inorganic porous material that comes into contact with a conductive liquid when introduced into the liquid reservoir, (b) an electrode accommodated in the electrode vessel, noble metal chloride NmCl layer being formed on the surface of the noble metal (referred to as "Nm"), and (c) an electrode solution filled in the electrode vessel, the noble metal chloride NmCl and an alkali metal chloride being dissolved therein at a saturated concentration.

(Constitution of Second Invention)

The constitution of a second invention to achieve the above objects resides in the planar patch clamp device according to the first invention, wherein the liquid reservoir on the first surface side includes a primary liquid reservoir for cell placement, made of a light non-transmissive material, a secondary liquid reservoir provided with an electrode section on the first surface side, and a narrow liquid path that communicates between the primary liquid reservoir and the secondary liquid reservoir.

(Constitution of Third Invention)

The constitution of a third invention to achieve the above objects is the planar patch clamp device according to the first or second invention, wherein the liquid reservoir on the second surface side is communicated with a liquid path to introduce and discharge a conductive liquid, and an electrode section on the second surface side is disposed on this liquid path.

(Constitution of Fourth Invention)

The constitution of a fourth invention to achieve the above objects resides in the planar patch clamp device according to any one of the first to third inventions, wherein a plurality of liquid reservoirs are disposed on the first surface side, and a recess having a width larger than that of a cell body of a nerve cell and having a depth that can inhibit the movement of a cultured cell body is formed in these liquid reservoirs.

(Constitution of Fifth Invention)

The constitution of a fifth invention to achieve the above objects resides in the planar patch clamp device according to any one of the first to fourth inventions, including the following constitution(s) (A) and/or (B):

(A) a liquid reservoir on the second surface side is communicated with a liquid suction device, thereby enabling negative pressure load on the liquid reservoir on the second surface side, and (B) an extracellular matrix-forming substance having cell fixing capability is attached on the circumference of the opening on the first surface side of a through hole on a substrate.

(Constitution of Sixth Invention)

The constitution of a sixth invention to achieve the above objects resides in an electrode section for planar patch clamp device, including the following constituents (a') to (c'):

(a') an electrode vessel, wherein at least part of a vessel wall is made of an inorganic porous material, (b') an electrode accommodated in the electrode vessel, noble metal chloride NmCl layer being formed on the surface of the noble metal Nm, and (c') an electrode solution filled in the electrode vessel, the noble metal chloride NmCl and an alkali metal chloride being dissolved therein at a saturated concentration.

(Constitution of Seventh Invention)

The constitution of a seventh invention to achieve the above objects resides in the electrode section for planar patch clamp device according to the sixth invention, wherein the inorganic porous material composing at least part of the vessel wall is porous glass or porous ceramic.

(Constitution of Eighth Invention)

The constitution of an eighth invention to achieve the above objects resides in the electrode section for planar patch clamp device according to the sixth or seventh invention, wherein a noble metal Nm is silver Ag or platinum Pt, and an alkali metal chloride is potassium chloride KCl.

(Constitution of Ninth Invention)

The constitution of a ninth invention to achieve the above objects resides in the electrode section for planar patch clamp device according to any one of the sixth to eighth inventions, wherein an electrode is the following (c) or (D):

(C) a stick electrode protruding inside an electrode vessel, a noble metal chloride NmCl layer being formed on the surface of a core made of the noble metal Nm, or (D) a cylindrical electrode formed on the inner periphery of an electrode vessel wall, wherein the bottom layer on the vessel wall side is a deposited layer of a noble metal Nm and the surface layer in contact with an electrode solution is a deposited layer of a noble metal chloride NmCl.

(Constitution of Tenth Invention)

The constitution of a tenth invention to achieve the above objects resides in a cell ion channel current measurement method, which includes introducing a conductive liquid into a liquid reservoir on a second surface side of the planar patch clamp device according to any one of the first to fifth inventions, and introducing a conductive liquid containing a cell to be measured dispersed therein into a liquid reservoir on the first surface side to conductively communicate between the liquid reservoir on first surface side and the liquid reservoir on the second surface side; disposing the cell at a prescribed position of the liquid reservoir on the first surface side; applying a voltage between electrodes of electrode sections on the first surface side and second surface side; and measuring an ion channel current of a cell to be measured.

(Constitution of Eleventh Invention)

The constitution of an eleventh invention to achieve the above objects resides in the cell ion channel current measurement method according to the tenth invention, wherein a plurality of liquid reservoirs of the constitution mentioned in the fourth invention are disposed on the first surface side of a substrate in the planar patch clamp device and a cell to be measured is a nerve cell, and a conductive liquid is a cell culture medium of the nerve cell.

(Constitution of Twelfth Invention)

The constitution of a twelfth invention to achieve the above objects resides in the cell ion channel current measurement method according to the eleventh invention, wherein a Ca probe for Ca imaging is introduced into a nerve cell in advance, and an ion channel current of the cell is measured by means at least including Ca imaging, which is observation of fluorescence that occurs at generation of cell action potential or at propagation of an action potential.

(Constitution of Thirteenth Invention)

The constitution of a thirteenth invention to achieve the above objects resides in the cell ion channel current measurement method according to the twelfth invention, wherein plural or many nerve cells into which a Ca probe introduced are disposed on the first surface side in the planar patch clamp device, and synapses of these nerve cells mutually linked are defined as a nerve cell network, and a current is injected or a voltage is applied to a single nerve cell of these cells to perform measurement by the Ca imaging in plural or many nerve cells.

Advantageous Effects of Invention

According to the first invention, the planar patch clamp device enables high-throughput screening by multipoint measurement, which is popular in a planar patch clamp device, and furthermore, suppresses variations in an applied membrane potential in a planar patch clamp device to reduce a noise current, thereby enabling accurate measurement of an ion channel current.

In an attempt to accurately measure a cell ion channel current, it is effective and important to establish measures against a noise current in the case of a low seal resistance in a planar patch clamp device as well as even in the case of not a low seal resistance. As measures against a noise current, it is effective to increase a seal resistance and suppress variations in an applied membrane potential on an electrode side.

When an electrode in which a noble metal chloride NmCl layer (for example, AgCl layer) on the surface of the noble metal Nm (for example, silver Ag) is formed is used as an electrode in a planar patch clamp device, such variations in an applied membrane potential as mentioned above is mainly due to variations in a phase boundary potential between the surface of the AgCl/Ag electrode and a solution surrounding it or variations in a phase boundary potential at a liquid/liquid interface.

Like the first invention, when an AgCl/Ag electrode within an electrode vessel in the electrode section is immersed into an electrode solution, a saturated solution of AgCl and alkali metal chloride (for example, KCl), and these are made contact with a conductive liquid such as cell culture medium (KCl concentration is about a few mM) via a vessel wall composed of an inorganic porous material, the interior and exterior of the electrode vessel becomes conductively communicated. However, since liquid itself hardly passes through a pore of the inorganic porous material, mixture of the electrode solution in the interior of the electrode vessel with the conductive liquid in the exterior of the electrode vessel is virtually ignored. As a result, large differences in concentrations of KCl between the interior and exterior of the electrode vessel is kept constant, and a phase boundary potential of the AgCl/Ag electrode or a phase boundary potential at a liquid/liquid interface is constant, resulting in no variations in an applied membrane potential.

According to the second invention, when a channel current is controlled by light using a cell expressing an ion channel that is opened by light, even when a primary liquid reservoir for cell placement in a liquid reservoir on the first surface side is irradiated with light, the irradiated light does not substantially reach the secondary liquid reservoir communicated via a narrow liquid path with the primary liquid reservoir, thus a trouble due to the irradiated light to an electrode section on the first surface side is prevented. In addition, an electrode solution slightly leaked from the electrode vessel of the electrode section hardly reaches the circumference of a cell disposed on the primary liquid reservoir by a barrier of the narrow liquid path. Therefore, variations in an applied membrane potential mentioned above according to the first invention are further prevented thoroughly. Considering this point, a liquid path that communicates between the primary liquid reservoir and the secondary liquid reservoir particularly preferably has an inner diameter of, for example, 1 mm or less.

According to the third invention, a conductive liquid for a liquid reservoir on the second surface side can easily and certainly be introduced and discharged; furthermore, when a channel current is controlled by light using a cell expressing an ion channel that is opened by light, even if a primary liquid reservoir on the first surface side is irradiated with light, since an electrode section on the second surface side is disposed on a liquid path separated from a liquid reservoir on the second surface side, a trouble due to the irradiated light to an electrode section on the second surface side is prevented.

According to the fourth invention, since a recess with a width larger than that of the cell body of a nerve cell and with a depth that can inhibit the movement of a cultured cell body is formed as a cell body placement area, once a nerve cell is disposed on this recess, the cell cannot move from the site even under culture conditions.

In the fourth invention, it is also possible that a plurality of recesses are connected each other with a groove smaller than a cell body. In this case, a plurality of cultured nerve cells can mutually form a two-dimensional network along a groove with a small width. As a result, an ion channel current of each nerve cell that formed a two-dimensional network can be measured with a high temporal and spatial resolution. More preferably, it can be performed by simultaneous multipoint measurement.

In a planar patch clamp device provided with the constitution (A) of the fifth invention, by loading negative pressure on a liquid reservoir on the second surface side using a liquid suction device, a conductive liquid can be sucked from a liquid reservoir on the first surface side via a fine through hole on a substrate. Therefore, a cell dispersed into the conductive liquid can be fixed to the opening of a through hole; in addition, the adhesion between a cell membrane and an extracellular matrix 18-applied surface is improved and a seal resistance is improved. In a planar patch clamp device provided with the constitution (B) of the fifth invention, by an extracellular matrix-forming substance, a cell dispersed into a conductive liquid on the first surface side can be fixed to the opening of a through hole. In this case, a stress that can affect cell ion channel activity is not added in a process in which a cell is trapped at a prescribed position of the planar patch clamp device.

In a planar patch clamp device of the fifth invention, the constitution (A) may be provided or the constitution (B) may be provided, while the constitutions (A) and (B) may be simultaneously provided.

According to the sixth invention, a new and useful electrode section for planar patch clamp device to be incorporated into a planar patch clamp device according to the first to fifth inventions are provided. The effects are as mentioned for the first invention.

According to the seventh invention, a preferable embodiment of an inorganic porous material composing at least part of the electrode vessel wall of an electrode section for planar patch clamp device is provided.

According to the eighth invention, a preferable embodiment of a noble metal used for an electrode of an electrode section for planar patch clamp device is provided.

According to the ninth invention, a preferable embodiment of shape and structure of an electrode of an electrode section for planar patch clamp device is provided.

According to the tenth invention, a new cell ion channel current measurement method using a planar patch clamp device according to any one of the first to fifth inventions is provided. The effects of this method are as mentioned for the first to fifth inventions; in other words, the maximum effect is that variations in an applied membrane potential in the planar patch clamp device are suppressed to reduce a noise current, thereby enabling accurate measurement of an ion channel current.

According to the eleventh invention, in a cell ion channel current measurement method according to the tenth invention, a superior ion channel current measurement method using a nerve cell is provided; especially, an ion channel current of each nerve cell that formed a two-dimensional network can be measured with a high temporal and spatial resolution, and furthermore, it can be performed by simultaneous multipoint measurement.

According to the twelfth invention, in addition to accurate measurement of an ion channel current as in the tenth and eleventh inventions, a great advantage that Ca imaging that is important for function analysis of a nerve cell or its network can be performed using a space above the substrate in the planar patch clamp device can be obtained.

According to the thirteenth invention, a single nerve cell (first nerve cell) on a fine through hole of a substrate in the planar patch clamp device is stimulated by current injection or voltage application to enable generation of an action potential; simultaneously, the action potential is propagated to the neighboring nerve cell (second nerve cell) via a nerve cell network; and furthermore, how the action potential is propagated from the second nerve cell to the neighboring third nerve cell can be measured by Ca imaging. As a prior art, for example, there is an electrode stimulation method; in the case of this method, it is difficult to selectively stimulate a single nerve cell, and analysis becomes complicated. In a micropipette electrode stimulation, another prior art, although a single nerve cell can be selectively stimulated, it is difficult to realize multichannel, which is required for high-throughput screening; according to the thirteenth invention, multichannel can easily be realized since a measurement part can be highly miniaturized.

REFERENCE SIGNS LIST

1 Substrate
2, 3 Spacer
4, 5 Plate
6 Primary liquid reservoir
7 Secondary liquid reservoir
8 Liquid path
9 Liquid reservoir
10 Liquid path for introduction
11 Liquid path for discharge
12 Cell
12a First nerve cell
12b Second nerve cell
13 Electrode vessel
14 Electrode solution
15 AgCl/Ag electrode
16 Inorganic porous material
17 Electrode pin
18 Extracellular matrix-forming substance
19 Through hole
20 Seal material
21 Suction tube
22 Negative pressure measurement manometer
23 Suction pump
24 Recess

DESCRIPTION OF EMBODIMENTS

Embodiments of the present invention, including best modes thereof, will be described below. The technical scope of the present invention is not limited by these embodiments.

[Planar Patch Clamp Device]

In a planar patch clamp device according to the present invention, a fine through hole that communicate between the first surface side (surface side for cell placement) and the second surface side, which are both sides in its electrically insulative substrate, is provided. In Examples, a dual-oriented planar patch clamp device in which a substrate is horizontally directed is shown; however, a device in which a substrate is directed in other directions, for example, a portrait-oriented planar patch clamp device in which a substrate is vertically provided is also included in the present invention.

It is possible to preferably use, as an electrically insulative substrate, a glass, ceramics or plastic substrate. As an example, when a silicon substrate is used, a silicon substrate (SOI substrate) having a structure in which a silicon layer on the first surface side, an oxidized silicon layer in the middle, and a silicon layer on the second surface side are laminated in this order is preferable. In a silicon substrate having such laminated structure, since an extremely high-insulative middle layer exists between two silicon layers, a high-resistance state can be established at the time of closure of an ion channel of a cell to be measured, and a background noise can be reduced.

There is no limitation on the number of through holes disposed on the substrate and the number of through holes may be one, and plural or many holes (for example, two to tens of holes or more) are particularly preferable. An inner diameter of a fine through hole is preferably one through which a liquid can pass but a cell cannot pass (for example, about 1 to 3 μm), but is not limited to such inner diameter.

In a planar patch clamp device according to the present invention, both the first surface side and the second surface side of the through hole are provided with a liquid reservoir that holds a conductive liquid and an electrode section disposed so that it is capable of energized for a conductive liquid in the liquid reservoir.

There is no particular limitation on the constitution of the liquid reservoir as long as it is possible to meet a demand that the liquid reservoir "holds a conductive liquid and an electrode section can be disposed energizably for a conductive liquid". For example, as shown in Examples, it can be formed by stacking a spacer member or plate member on both the first surface side and the second surface side of a substrate, and providing a notch for the spacer member at a site corresponding to a through hole on the substrate.

Although not necessarily limited, a spacer member and a plate member on the first surface side are preferably made of a light non-transmissive material, and a spacer member and a plate member on the second surface side are preferably made of a light transmissive material.

The liquid reservoir per se is formed in a liquid-tight state and is equipped with a liquid path to introduce or discharge a conductive liquid (or a conductive liquid in which a cell is dispersed) or an openable/closable opening. When a planar patch clamp device is a landscape-oriented type in which a substrate is horizontally directed, the upper part of a liquid reservoir on the first surface side of a substrate may be covered with a member for lid such as cover glass and, as needed, the member for lid may be removed to open the liquid reservoir.

In the planar patch clamp device according to the present invention, an electrode section with a new constitution are provided on the first surface side and the second surface side; this point will be mentioned later in the item of "Electrode Section for Planar Patch Clamp Device".

Furthermore, the planar patch clamp device according to the present invention preferably has such constitution that a liquid reservoir on the first surface side includes a primary liquid reservoir for cell placement made of a light non-transmissive material, a secondary liquid reservoir in which an electrode section on the first surface side is disposed, and a narrow liquid path that communicates between these liquid reservoirs. The constitution is also preferably that a liquid reservoir on the second surface side is communicated with a liquid path to introduce and discharge a conductive liquid and that an electrode section on the second surface side is disposed on this liquid path. Particularly preferably, a plurality of liquid reservoirs are disposed on the first surface side, and a recess with a width larger than that of a cell body of a nerve cell and with a depth that can inhibit the movement of a cultured cell body can be formed in these liquid reservoirs. Furthermore, it is also possible that these plural recesses are mutually communicated with a groove with a width smaller than that of a cell body. It is preferable that a planar patch clamp device includes the following constitutions (A) and/or (B):

(A) a liquid reservoir on the second surface side is communicated with a liquid suction device, thereby enabling negative pressure load on the liquid reservoir on the second surface side, and (B) an extracellular matrix-forming substance having cell fixing capability is attached on the circumference of the opening on the first surface side of a through hole on a substrate.

Examples of a constituent material of the above extracellular matrix-forming substance include polylysine, collagen (type I, type II, type IV), proteoglycan, fibronectin, laminin, collagen, proteoglycan (e.g., versican, decorin), proteoglycan (aggrecan), link protein, entactin, tenascin, proteoglycan [chondroitin sulfate proteoglycan, heparan sulfate proteoglycan (e.g., perlecan), keratan sulfate proteoglycan, dermatan sulfate proteoglycan], hyaluronic acid (a type of glycosaminoglycan), elastin, fibrin, and the like.

[Electrode Section for Planar Patch Clamp Device]

Furthermore, an electrode section for planar patch clamp device according to the present invention includes the following constituents (a') to (c'), and are disposed on the first surface side and the second surface side:

(a') an electrode vessel, wherein at least part of a vessel wall is made of an inorganic porous material, (b') an electrode accommodated in the electrode vessel, noble metal chloride NmCl layer being formed on the surface of the noble metal Nm, and (c') an electrode solution filled in the electrode vessel, the noble metal chloride NmCl and an alkali metal chloride being dissolved therein at a saturated concentration.

There is no limitation on the type of the above noble metal Nm, and the metal is preferably silver Ag or platinum Pt, and particularly preferable silver Ag. Therefore, the noble metal chloride NmCl is preferably silver chloride AgCl or platinum chloride AgCl, and particularly preferably silver chloride AgCl. There is no limitation on an alkali metal chloride, and the alkali metal chloride is preferably potassium chloride KCl. An inorganic porous material composing at least part of the vessel wall is preferably porous glass or porous ceramic.

It is also preferable that an electrode in the electrode section is the following (C) or (D):

(C) a stick electrode protruding inside an electrode vessel, a noble metal chloride NmCl layer being formed on the surface of a core made of the noble metal Nm, or (D) a cylindrical electrode formed on the inner periphery of an electrode vessel wall, wherein the bottom layer on the vessel wall side is a deposited layer of a noble metal Nm and the surface layer in contact with an electrode solution is a deposited layer of a noble metal chloride NmCl.

[Cell Ion Channel Current Measurement Method]

A cell ion channel current measurement method according to the present invention is a method which includes using a planar patch clamp device according to various modes mentioned above, introducing a conductive liquid into a liquid reservoir on a second surface side of the planar patch clamp device, and introducing a conductive liquid containing a cell to be measured dispersed therein into a liquid reservoir on the first surface side to conductively communicate between the liquid reservoir on first surface side and the liquid reservoir on the second surface side; disposing the cell at a prescribed position of the liquid reservoir on the first surface side; applying a voltage between electrodes of electrode sections on the first surface side and second surface side; and measuring an ion channel current of a cell to be measured.

In this case, an especially characteristic embodiment is that a plurality of liquid reservoirs are disposed on the first surface side of a substrate in the planar patch clamp device, a cell to be measured is a nerve cell, and a conductive liquid is a cell culture medium of the nerve cell.

(Ca Imaging)

There is no particular limitation on means or systems to measure a cell ion channel current, and, for example, usual current measurement can be performed, and more preferable means include Ca imaging (calcium imaging). Ca imaging is especially effective in analysis of plural or many nerve cell networks.

As is well known, Ca imaging is a method wherein a dye that binds to Ca ions to show a fluorescence (referred to as "Ca fluorescent indicator" or "Ca probe") is introduced into a cell, and a phenomenon in which Ca ions enter the cell body when an action potential is generated in a nerve cell is detected as a fluorescence.

The reason that Ca imaging is effective for ion channel current measurement of a cell, especially nerve cell, is as mentioned in connection with the twelfth and thirteenth inventions in the item of aforementioned "Advantageous Effects of Invention".

EXAMPLES

Examples of the present invention will be described below. The technical scope of the present invention is not limited by the following examples.

First Example

Figure 1:
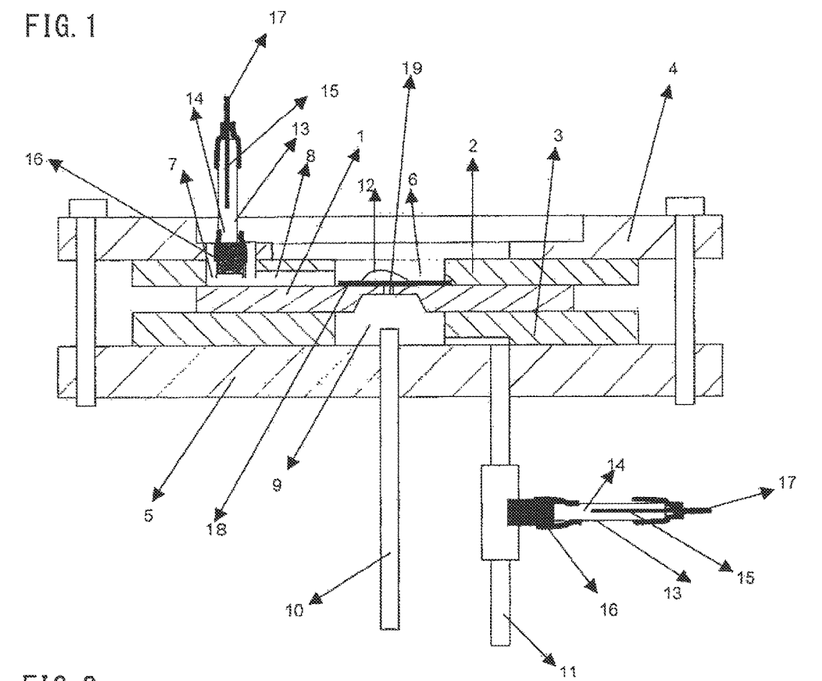
FIG. 1 is a section view showing a planar patch clamp device according to First Example.

A planar patch clamp device according to the present Example is shown in FIG. 1. This device is an incubation type planar patch clamp device that serves as an ion channel biosensor.

As an electrically insulative substrate 1 in the planar patch clamp device, a silicon substrate is used (Non Patent Literature 1). In FIG. 1, while a single planar patch clamp device is formed on a substrate 1, many planar patch clamp devices may be formed using a substrate 1 with a larger area.

Provided on the substrate 1 is a fine through hole 19 with a diameter of 1 to 3 μm that communicate between its first surface side (the upper side of the drawing) and its second surface side (the lower side of the drawing). While one through hole 19 is provided in the center of a substrate 1 in FIG. 1, many through holes 19 may be provided using a larger substrate and the following constituted may be imparted to each through hole 19 may be constituted in the following manner. A cell 12 is disposed on the opening on the first surface side of a through hole 19.

The first surface side and the second surface side of a substrate 1 are sandwiched with a pair of spacers 2 and 3. There is no limitation on the constituent material of spacers 2 and 3. However, as for a spacer 2 on the first surface side, preferably an elastic light non-transmissive material, for example, silicone rubber or polydimethylsiloxane (PDMS) can be used. On the other hand, as for a spacer 3 on the second surface side, preferably a light transmissive material can be used.

On a placement portion of the cell 12 in a spacer 2, for example, a circular notch is disposed. A cell 12 is provided on this notch. Also in a spacer 3, for example, a circular notch is disposed on a portion corresponding to a spacer 2, and the opening on the second surface side in a through hole 19 opens into this notch.

The whole of the above substrate 1 and a pair of spacers 2 and 3 is tightened with a pair of strong plates 4 and 5. There is no particular limitation on the material of plates 4 and 5 as long as it resists autoclave sterilization at about 120° C. However, as for a plate 4 on the first surface side, preferably a light non-transmissive material can be used. On the other hand, as for a plate 5 on the second surface side, preferably a light transmissive material can be used.

In the above constitutions, in the center of a plate 4 on the first surface side, for example, a circular notch of a similar size is provided at a similar site, corresponding to the above notch of a spacer 2 on the first surface side. A recess-shaped step portion with a thin plate may be formed on the circumference of a notch disposed in the center of a plate 4 and a member for lid such as cover glass (not shown) may be disposed on this step portion, thereby enabling opening/closing of the opening of the above notch in a spacer 2. In this way, a primary liquid reservoir 6 is formed on the first surface side.

On the other hand, by covering the opening of a notch in a spacer 3 on the second surface side with a plate 5, a liquid reservoir 9 is formed on the second surface side. A primary liquid reservoir 6 disposed on the first surface side and a liquid reservoir 9 on the second surface side are communicated via a through hole 19.

A primary liquid reservoir 6 composes a first region of a liquid reservoir on the first surface side; a space that communicated via a narrow liquid path 8 disposed on a spacer 2 for this primary liquid reservoir 6 is a secondary liquid reservoir 7 comprising a second region of a liquid reservoir on the first surface side. The secondary liquid reservoir 7 is formed by a hole commonly disposed on a spacer 2 and a plate 4. On the secondary liquid reservoir 7, an electrode section on the first surface side, which is mentioned later, is disposed.

A conductive liquid is introduced and held in a liquid reservoir on the first surface side comprised by a primary liquid reservoir 6, a liquid path 8, and a secondary liquid reservoir 7. In this conductive liquid, a cell to be measured can be dispersed. As a conductive liquid to be introduced, a buffer such as 140 mM NaCl, 3 mM KCl, 10 mM 4-(2-hydroxyethyl)-1-piperazineethanesulfonic acid (HEPES), 2.5 mM $CaCl_2$, 1.25 mM $MgCl_2$, and 10 mM glucose at pH 7.4 (with HCl), or a cell culture medium of Dulbecco's modified Eagle's medium (DMEM: Sigma) added with 10% (v/v) FBS and 1% (v/v) Glutamax™ (Gibco), etc. is used.

The composition of these conductive liquids is appropriately changed depending on the type of a cell.

Into a liquid reservoir 9 on the second surface side, a buffer called pipette solution such as 40 mM CsCl, 80 mM CsCH$_3$SO$_4$, 1 mM MgCl$_2$, 10 mM HEPES, 2.5 mM MgATP, 0.2 mM Na$_2$EGTA (pH 7.4), or a cell culture medium, etc. is introduced. Introduction of a conductive liquid into the liquid reservoir 9 is performed with a tubelike liquid path for introduction 10, and discharge of it is performed with a liquid path for discharge 11. In this example, a PEEK tube with an outer diameter of 1 mm and an inner diameter of 0.5 mm is used as a liquid path for introduction 10 and a liquid path for discharge 11, but also as for a constituent material for these liquid paths, other materials can be used as long as they resist autoclave sterilization at about 120° C.

Also on a liquid path for discharge 11, an electrode section on the second surface side with a similar constitution to an electrode section on the first surface side is disposed. Usually, an electrode of the electrode section on the first surface side is grounded, and a membrane voltage is applied to an electrode of the electrode section on the second surface side.

When a conductive liquid in which a cell 12 is dispersed is introduced into a primary liquid reservoir 6, in order to place a cell 12 to the opening site of a through hole 19 shown in FIG. 1, for example, as mentioned later in Second Example, if a conductive liquid in a liquid reservoir 9 is sucked by a liquid suction device communicated with a liquid reservoir 9 on the second surface side, a conductive liquid in a primary liquid reservoir 6 is also sucked via a through hole 19, thus a cell 12 is disposed to the above site. Furthermore, in this case, a fine hole can be formed on the cell membrane of a cell 12 in the part contacting a through hole 19 by suction pressure. In order to form such hole on a cell membrane, there is also a method that a solution in which a cell membrane-perforating antibiotic such as nystatin and amphotericin B is dissolved is introduced from a liquid path for introduction 10 into a liquid reservoir 9 on the second surface side. When such hole is formed on a cell membrane, the inside of a cell and a liquid reservoir 9 on the second surface side become conductively communicated (Non Patent Literature 1).

On the other hand, in the case of an incubation type planar patch clamp device, as means to place a cell 12 to the opening site of a through hole 19 shown in FIG. 1, an extracellular matrix-forming substance 18 having cell fixing capability may be attached on the circumference of the opening on the first surface side in a through hole 19 of a substrate 1.

In the above constitutions, a prescribed ion channel is expressed in a cell 12, and when a stimulator that opens the ion channel is added to a liquid reservoir on the first surface side, the ion channel is opened and a channel current depending on an applied voltage flows between an electrode section on the first surface side and an electrode section on the second surface side. At this time, if there is a gap between the cell membrane of a cell 12 and a substrate 1, a seal resistance is reduced and a leak current is superimposed on a channel current.

As for a membrane potential, since an induced voltage due to an electromagnetic wave existing in a space, a phase boundary potential between the surface of an electrode metal and its surrounding buffer, or a phase boundary potential at a liquid/liquid interface is superimposed on an actually applied voltage between electrode, a leak current varies by variations in an induced noise or a phase boundary potential. Therefore, a noise of variations in baseline occurs for an ion channel current. These baseline variation noise current and ion channel current are represented in FIG. 2 as a function of a seal resistance and a membrane potential variation voltage DVm.

Figure 2:
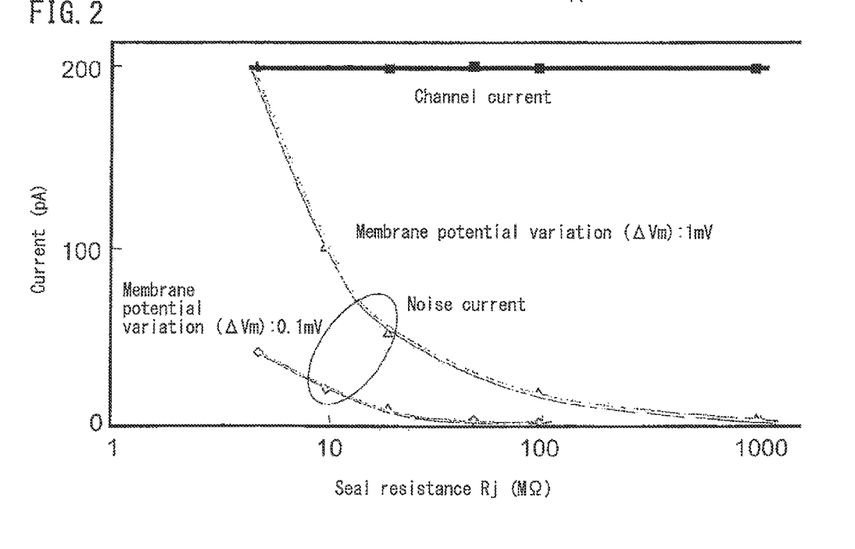
FIG. 2 is a graph showing a noise current and ion channel current as a function of a seal resistance and a membrane potential variation voltage $\Delta$Vm.

As is apparent from FIG. 2, in a pipette patch clamp in which a seal resistance of giga ohm or more can easily be obtained, effects of a baseline variation noise are negligible even if a membrane potential variation DVm is relatively large; while in an incubation type planar patch clamp in which a seal resistance is relatively small (≤10 MΩ), this membrane potential variation DVm needs to be small. The present invention provide a planar patch clamp technology that enables measurement with a small noise current even if a seal resistance is small, by developing an electrode in which variations in a membrane potential is small and stable and by making DVm greatly small.

Figure 3:
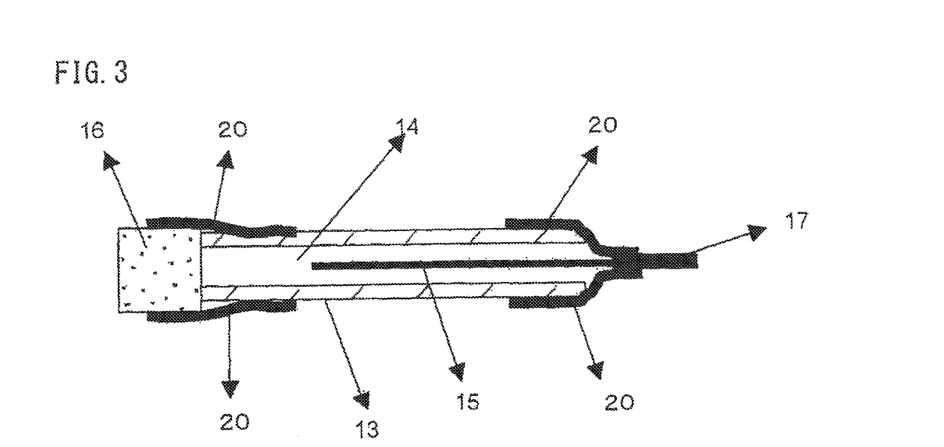
FIG. 3 is a section view showing a detailed structure of an electrode section according to First Example.

A detailed structure of electrode sections on the first surface side and the second surface side is shown in FIG. 3. The interior of a cylindrical electrode vessel 13 with an inner diameter of 1 mm made of a PYREX (registered trademark) glass is filled with an electrode solution 14 containing KCl and AgCl dissolved therein at a saturated concentration. KCl concentration is 3.3 M/L and AgCl of about 1.1 mM/L is added. In the case of KCl, a saturated concentration is about 3.3 M/L at normal temperature. In an AgCl/Ag electrode 15 accommodated in an electrode vessel 13, the surface of a silver wire is coated with AgCl. Such AgCl/Ag electrode 15 can be formed by applying an AgCl powder to the surface of a silver wire, or can be fabricated by immersing a silver wire into a bleach, etc. containing sodium hypochlorite. Also, such AgCl/Ag electrode can be fabricated by electroplating within a KCl solution.

The tip of electrode vessel 13 is covered with an inorganic porous material 16 such as porous glass and porous ceramics. As an inorganic porous material 16, actually a Vycor glass (Corning Incorporated) was used. The tip of an inorganic porous material 16 composing part of the vessel wall of an electrode vessel 13 in this way is immersed into a conductive liquid (cell culture medium or buffer). Although KCl concentration in a conductive liquid is a few mM, effects of this inorganic porous material 16 lead to a negligible mixture of an electrode solution 14 with a conductive liquid outside the vessel while the inside and outside of the vessel of an electrode vessel 13 are conductively communicated, resulting in a constant large difference in KCL concentration between the inside of the vessel and the outside of the vessel; as a result, a phase boundary potential of AgCl/Ag electrode 15 or a phase boundary potential at a liquid/liquid interface remains constant. The base end of an electrode vessel 13 is sealed with a seal material 20, from which an electrode pin 17 protrudes.

Figure 4:
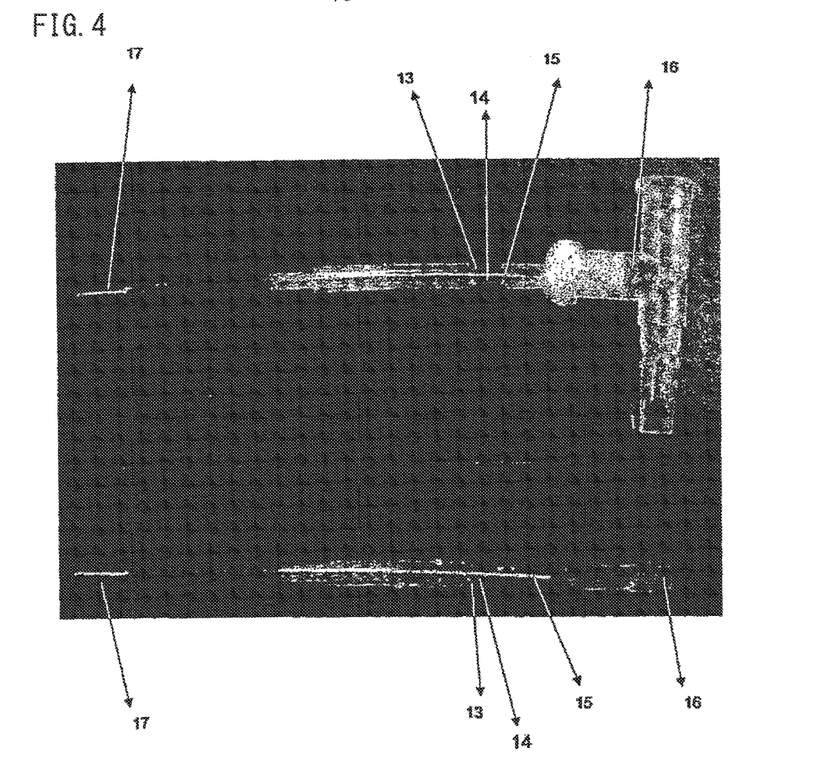
FIG. 4 is a photograph showing an electrode section actually fabricated in First Example.

A photograph of an actually fabricated electrode portion is shown in FIG. 4. A photograph of the upper side of FIG. 4 is an electrode section on the second surface side; a pipe joint for connection with a liquid path for discharge 11 shown in FIG. 1 is assembled to the electrode section, and an inorganic porous material 16 is exposed within the pipe line of the pipe joint. A photograph of the lower side of FIG. 4 is an electrode section on the first surface side, and as shown in FIG. 1, the electrode section is disposed on a secondary liquid reservoir 7.

When a channel current is controlled using a cell expressing an ion channel that is opened by light, if electrode sections on the first surface side and the second surface side are disposed as mentioned above, a liquid reservoir on the first surface side is formed by a light non-transmissive spacer 2 or plate 4; thus, an AgCl/Ag electrode of electrode sections on the first surface side and the second surface side is not irradiated with an irradiated light to a primary liquid reservoir 6. Since a cell is disposed on the primary liquid reservoir 6 and a potassium ion concentration of a conductive liquid outside the cell is as small as about a few mM, it is desirable to minimize the effects of KCl leaked from an electrode section although the amount is small. Therefore, as for a liquid reservoir on the first surface side, a secondary liquid reservoir 7 is fabricated, in addition to a primary liquid reservoir, and these primary liquid reservoir 6 and secondary liquid reservoir 7 are communicated with a narrow liquid path 8 with a width of 1 mm or less.

Figure 5:
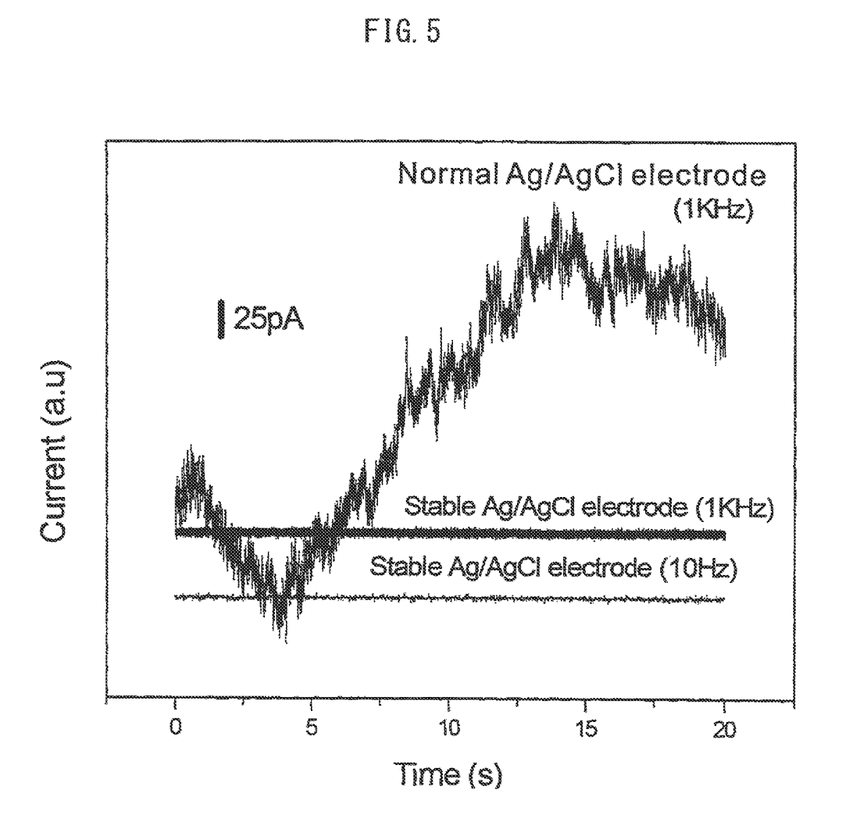
FIG. 5 is a graph showing the measurement result of current variations at an applied voltage of 0 mV when a conventional AgCl/Ag electrode (referred to as "normal AgCl/Ag electrode") is used and that an electrode section of the present invention (referred to as "stable AgCl/Ag electrode") is used.

In order to examine the effects of an electrode section for planar patch clamp device according to the present invention, a result of comparison of current variations at an applied voltage of 0 mV when a conventional normal AgCl/Ag electrode is used and an electrode section of the present invention is used is shown in FIG. 5. By setting a silicon substrate with a through hole 19 with a diameter of about 2 μm to a planar patch clamp device in FIG. 1 and by not disposing a cell 12, a current variation is measured at an applied voltage 0 mV. Since the resistance of a through hole 19 is about 2 MΩ, a slow phase boundary potential variation of about 0.5 mV is observed in a conventional AgCl/Ag electrode, leading to great variations in baseline; in contrast, in an electrode section of the present invention, a phase boundary potential variation is negligible. The measurement was performed with Axopatch 200B (Molecular Devices, LLC). Values in parentheses in FIG. 5 represent frequency of low-pass filter of the Axopatch 200B at the time of measurement. As shown in the drawing, stabilization of an electrode of the present invention is extremely effective.

Second Example

Figure 6:
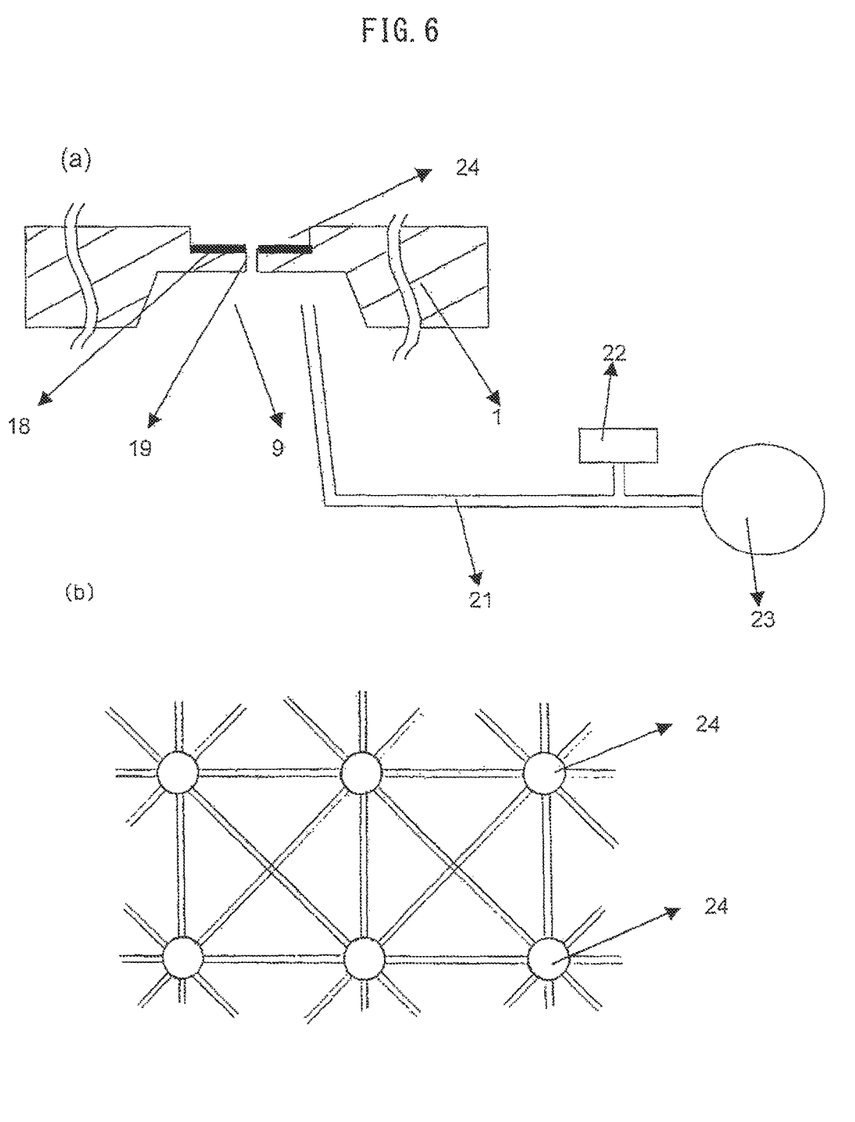
FIG. 6(a) is a section view showing the main section of a planar patch clamp device according to Second Example.
FIG. 6(b) is a plane view showing a plurality of circular recesses 24 and narrow grooves that mutually connect these portions.

The main section of a planar patch clamp device according to Second Example is shown in FIG. 6(*a*). Although the constitution of the device is basically same as that in FIG. 1, only the part near a fine through hole 19 of a substrate 1 has a different structure. In other words, a recess 24 with a width larger than that of a cell body and with a depth that can inhibit the movement of a cultured cell body is formed as a cell body placement region on the opening on the first surface side in a through hole 19 on a substrate 1.

In an incubation type planar patch clamp device, even if a cell is disposed on a through hole, the cell often moves during culture, and a seal resistance may vary and a cell may move out of the hole, resulting in malfunction of a sensor itself. In the present Example, a recess 24 slightly larger than the size of a cell is formed on the opening of a through hole 19 so that a cell cannot move during culture when disposed on this recess 24. Since the size of a normal cell is about 10 to 30 μm in major axis, the recess 24 may be a circular or rectangular planar shape with a size larger than the major axis of a cell such as 10 to 30 μm, although the size depends on the type of a cell. The depth of the recess is usually about 5 to 12 μm to sufficiently achieve the objective, although it also depends on the size of a cell. It is also preferable to apply an extracellular matrix-forming substance 18 having cell fixing capability to the bottom of the recess 24.

As an extracellular matrix-forming substance 18, poly-L-lysine, poly-D-lysine, or laminin, etc. is suitable for a nerve cell and PC12 cell, and collagen IV or fibronectin is suitable for a HEK293 cell.

For formation of the pattern of a recess 24 as mentioned above, when a substrate 1 is made of Si, glass, or ceramics, the pattern can easily be formed by coating a photoresist with a thickness corresponding to the depth of the recess 24 with a spinner and by exposing and developing the photoresist using a prescribed photomask. When a substrate 1 is made of a plastic, the pattern can easily be formed by hot embossing process or injection molding.

When a cell 12 to be measured is a nerve cell, in addition to a circular or rectangular recess 24, it is particularly preferable to form a narrow groove in which an axon and a dendrite can elongate so that the groove is extended from a recess 24 (for example, a plurality of narrow grooves are extended radially from the center of the recess 24). Furthermore, when a nerve cell is to be measured, it may especially be preferable to form a nerve cell network during culture by disposing a plurality of recesses 24 on a substrate 1, and mutually communicating these plural recesses 24 with the above narrow groove.

In the present Example, the planar patch clamp device has a structure that enables loading of negative pressure to a liquid reservoir 9 on the second surface side, by suction with a suction pump 23 through a suction tube 21 that communicated with a liquid reservoir 9 on the second surface side when a cell is disposed on a recess 24. On a prescribed part of the suction tube 21, a negative pressure measurement manometer 22 to measure this negative pressure is disposed. This suction tube 21 can serve as a liquid path for discharge 11 mentioned in First Example. Although it is not essential to dispose such suction device, if a suction device is disposed, negative pressure suitable for suction should be usually about 0.01 to 0.5 atmospheres by considering the type of a cell.

An example in which a recess 24 including the above narrow groove is formed is shown in FIG. 6(*b*). In this case, a recess 24 and a narrow groove were formed using a nickel mold of a grid-like pattern having a circular pattern with a diameter of 30 to 50 μm at an intersection of narrow grooves.

Actually, HEK293 cells were seeded while negative pressure of −0.2 to −0.5 atmospheres is loaded to a liquid reservoir 9 on the second surface side by suction with a suction pump 23 so that a HEK293 cell moves to the site of a through hole 19. At this time, cells were seeded at a site other than a recess 24, which is rather preferable in terms of cell culture. In this way, according to the present Example in which a recess 24 is formed, a highly stable ion channel current can be measured. Since the recess 24 aims to prevent the movement of a cell, its form is not limited to a rectangular cross-section shape in which the bottom is perpendicular to the side wall as shown in FIG. 6(*a*), and may be a cross-section shape in which the cross-section is semicircular or semielliptical (e.g., bowl-like).

Disposition of a suction pump 23 is also effective other than at the time of cell seeding. In other words, when suction is performed at the time of channel current measurement to apply negative pressure to a liquid reservoir 9 on the second surface side, a cell is pulled toward the liquid reservoir 9 via a fine through hole 19; as a result, the adhesion between a cell membrane and an extracellular matrix 18-applied surface is improved and a seal resistance is improved. Namely, there is an effect that a noise in ion channel current measurement can be reduced. Although the degree of improvement of this effect widely varies depending on the size of a cell or a relative relationship between the site of a through hole 19 and the site of a cell, an approximate appropriate value of negative pressure is 0.01 to 0.5 atmospheres, which improved a seal resistance by 2- to 10-fold.

Third Example

Using a substrate 1 provided with a recess 24 as mentioned above, and using an incubation type planar patch clamp device provided with a suction mechanism for liquid negative pressure application that communicated with a liquid reservoir 9 on the second surface side of the substrate 1 and with otherwise same constitution as shown in FIG. 1, a cell ion channel current was measured. As a substrate 1, the same silicon substrate as used in measurement shown in FIG. 5 was used. As a cell, (a) a C2C12 cell expressing channel rhodopsin 2 (ChR2) and (b) a HEK293 cell expressing channel rhodopsin wide receiver (ChR-WR) were used. For these ion channels, it is known that a channel is opened by blue light (ChR2: Philipp Schoenenberger et al., Brain Cell Biology 36 (2008) 119; ChR-WR: Hongxia Wang, et al., J. Biol. Chem., 284 (2009) 5685).

Figure 7:
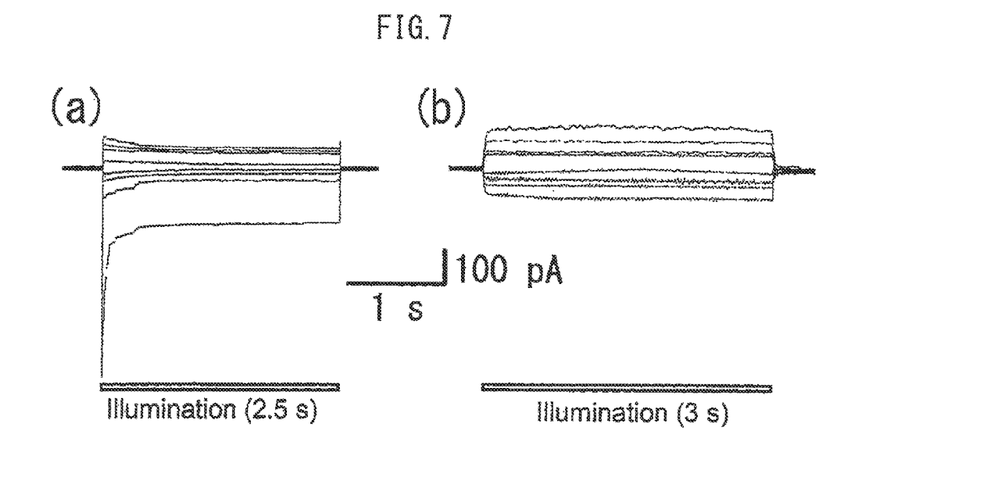
FIG. 7 is a view showing the measurement results of an ion channel current in Third Example.

As a light source for stimulation, a laser with a wavelength of 473 nm was used. In ascending order, applied membrane potentials for both (a) and (b) were −60, −30, −20, −10, 20, 30, 50, and 70 mV. An irradiated laser power was about 2 mW, and a laser beam was concentrated to a diameter of about 50 μm. As the result of measurement is shown in FIG. 7, in both cases of (a) and (b), effects of an electrode section according to the present invention resulted in successful channel current measurement with a good S/N ratio despite of a low seal resistance of 10 MΩ.

Fourth Example

Figure 8:
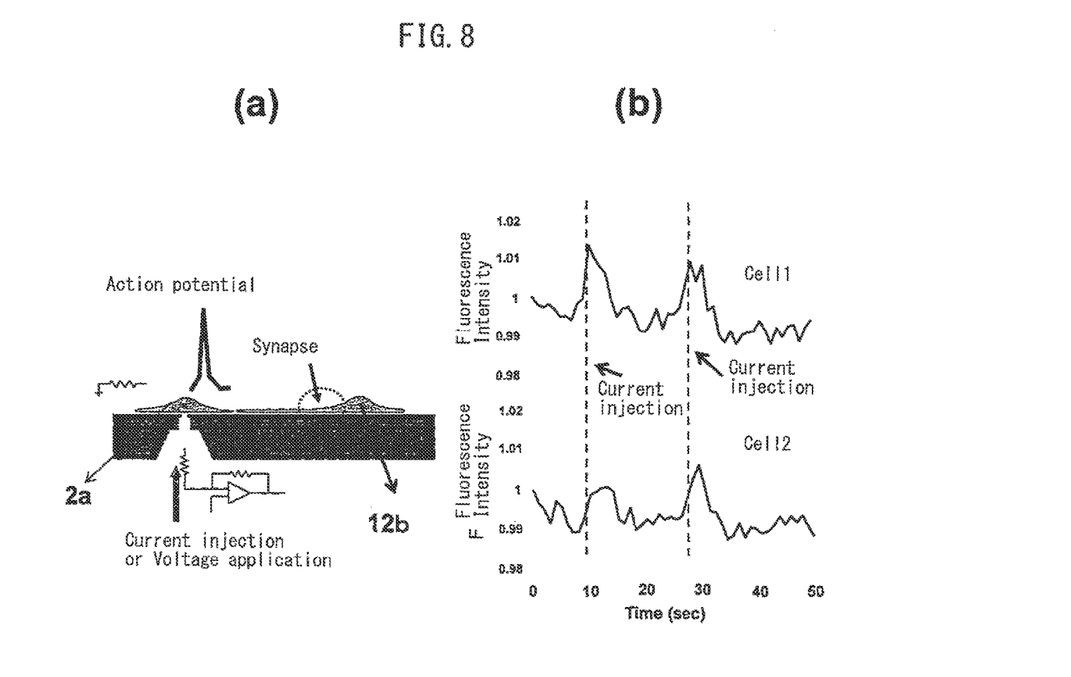
FIG. 8 is a view showing Fourth Example for Ca imaging of a nerve cell network.

Fourth Example of the present invention will be described based on FIG. 8. FIG. 8 (a) shows a front section view of a planar patch clamp device, and on the substrate representing a cross-section in the center of the drawing, a first nerve cell 12a on the left and a second nerve cell 12b on the right are illustrated. These nerve cells 12a and 12b are actually disposed within recesses 24, and recesses 24 were communicated via a narrow groove, but for convenience of illustration, a recess 24 and a narrow groove are not shown. Then, via a narrow groove (not shown), the first nerve cell 12a and the second nerve cell 12b are linked by an axon and a synapse.

By applying a voltage from a lower electrode (electrode on the second surface side), a stable AgCl/Ag electrode of the present invention, and by injecting a current to a first nerve cell 12a disposed on a fine through hole, an action potential is generated in the nerve cell 12a. This action potential is propagated to an axon, inducing the release of neurotransmitters at a synapse, the influx of ions by receipt of neurotransmitters by receptor proteins on the surface of a postsynaptic membrane, and then the generation of an action potential at a neighboring second nerve cell 12b. As a result of this, a series of events of Ca ion influx into the neighboring second nerve cell 12b and pulsatile emission of the fluorescence of a Ca probe introduced into the nerve cell in advance are observed.

In other words, this example is an example of application of system constitution in which using a device of the present invention, an action potential is generated in a first nerve cell 12a, and via an axon and a synapse, the propagation of this action potential is received at a neighboring second nerve cell 12b.

As a substrate in the planar patch clamp device, a polymethacrylate (PMMA) substrate including a fine through hole with a diameter of 2 microns on its surface was used. After the surface of the substrate was coated with poly-L-lysine, an extracellular matrix, nerve cells obtained from rat cerebral cortex were seeded on this surface at a density of $3 \times 10^2$ to $6 \times 10^3/mm^2$ to form a nerve cell network. Until the network is formed, liquid reservoirs in the upper part and the lower part of the substrate were filled with a medium of nerve cells and a Ca probe was introduced into a nerve cell, and at the time of current injection from a fine through hole, liquids in the upper part and the lower part were exchanged with an extracellular fluid buffer and an intracellular fluid buffer, respectively.

In the present Example, it is necessary that one of the nerve cells 12a is disposed on a fine through hole, as shown in FIG. 8(a). Other cells, for example, illustrated nerve cells 12b, etc. need not be disposed on a fine through hole, but may be disposed on a fine through hole as long as current injection or voltage application is not performed. The following thing is easily guessed from the basic constitution of the present invention: in the constitution in which a nerve cell 12b is also disposed on a fine through hole, if a stable electrode of the present invention is disposed on the upper part (first surface side) and the lower part (second surface side) of a substrate near the nerve cell 12b while the stable electrode is electrically insulated to a liquid reservoir on the nerve cell 12a side, an ion channel current is generated by effects of an action potential reached to the nerve cell 12b; thereby this current can easily be measured not only by Ca imaging but also as an ion channel current of the nerve cell 12b at the same time.

This nerve cell network is set so that it can be observed with a fluorescence microscope and an image observed with the microscope can be observed with a CCD camera. In this setting, a current pulse or a voltage pulse with a short pulse width is applied to an electrode on the lower side.

In the present Example, when a current with a pulse width of 1 millisecond and of 700 pA is injected from an electrode on the lower side to a nerve cell 12a on a fine through hole, an action potential is generated in this nerve cell 12a. A Ca probe for Ca imaging is introduced into nerve cells 12a and 12b in advance. In the present Example, a dye solution for Ca probe called Oregon Green Bapta-1 was introduced into a cell in a prescribed procedure. The same effects were obtained from other dyes for Ca imaging.

Since an action potential is generated in a nerve cell 12a on a fine through hole and Ca ion enters into this cell body, a pulsatile signal output shown in a graph with additionally inscribed "cell 1" in the upper part of the FIG. 8(b) was obtained as a CCD output. Furthermore, this action potential is propagated to the axon of the nerve cell 12a and is propagated to a neighboring nerve cell 12b via a synapse, inducing Ca ion influx in this cell. As a result, the fluorescence intensity of a Ca probe in this nerve cell 12b was instantaneously increased, and a signal of the nerve cell 12b (a lower graph with additionally inscribed "cell 2") that was synchronize with a signal in an upper graph with additionally inscribed "cell 1" was obtained.

The present example shows that the present invention can be applied to a high-throughput screening device for nerve cell network. Since signal propagation between nerve cells via an axon is a basic characteristic of a nerve cell network, performance evaluation of drugs involved in deterioration or recovery of this basic characteristic can be achieved with a system of the present Example. In addition, since a device of the present invention itself is a very smaller than a pipette patch clamp, multichannel, which is essential for the constitution of a high-throughput device, can easily be realized.

INDUSTRIAL APPLICABILITY

The present invention provides a planar patch clamp device that suppresses variations in an applied membrane potential to reduce a noise current, thereby enabling accurate measurement of a cell ion channel current.

More specifically, an incubation type planar patch clamp device is suitable for high-throughput screening of nerve cells requiring culture. Recently, the need for function analysis of a nerve cell network and high-throughput screening, especially the need for a device that uses channel current measurement has been internationally increased, but no successful cases have been reported (Jonathan Erickson et al., Journal of Neuroscience Methods, 175, (2008) 1-16, etc.). When an electrode section of the present invention is used for an electrode for current measurement of a planar patch clamp device for function analysis of a nerve cell network or a high-throughput screening device that measures an ion channel current using nerve cells, these devices can be realized, which has been difficult up to now.

The invention claimed is:

1. A planar patch clamp device comprising:
   (1) an electrically insulative substrate provided with one or more fine through holes, each having an inner diameter through which a cell cannot pass but a liquid can pass, the fine through holes communicating between surfaces on both sides of the electrically insulative substrate, wherein one side defines a first surface side, and the opposite side defines a second surface side;
   (2) a liquid reservoir and an electrode unit disposed on each of the first surface side and the second surface side of the through hole, the liquid reservoir holding a conductive liquid;
   (3) the liquid reservoir on the first surface side serving as a liquid reservoir for cell placement; and
   (4) the following constituents (a) to (c) included in the electrode units on the first surface side and the second surface side:
      (a) a closed or sealed electrode vessel enclosed with a vessel wall, at least part of which is made of an inorganic porous material,
      (b) an electrode accommodated in the closed or sealed electrode vessel, noble metal chloride NmCl layer being formed on the surface of the noble metal Nm, and
      (c) an electrode solution filled in the closed or sealed electrode vessel, the noble metal chloride NmCl and an alkali metal chloride being dissolved therein at a saturated concentration,
      wherein the inorganic porous material of the vessel wall separates the conductive liquid held in the liquid reservoir from the electrode solution filled in the closed or sealed electrode vessel, and enables an electrical communication, but minimizes a fluid communication between the electrode solution and the conductive liquid.

2. The planar patch clamp device according to claim 1, wherein the liquid reservoir on the first surface side includes
   a primary liquid reservoir for cell placement, made of a light non-transmissive material,
   a secondary liquid reservoir provided with the electrode unit on the first surface side, and
   a narrow liquid path that communicates between the primary liquid reservoir and the secondary liquid reservoir.

3. The planar patch clamp device according to claim 1, wherein
   the liquid reservoir on the second surface side is communicated with a liquid path to introduce and discharge a conductive liquid, and
   the electrode unit on the second surface side is disposed on this liquid path.

4. The planar patch clamp device according to claim 1, wherein
   a plurality of liquid reservoirs are disposed on the first surface side, and
   a recess having a width larger than that of a cell body of a nerve cell and having a depth that can inhibit the movement of a cultured cell body is formed in these liquid reservoirs.

5. The planar patch clamp device according to claim 1, including the following constitution(s) (A) and/or (B):
   (A) the liquid reservoir on the second surface side is communicated with a liquid suction device, thereby enabling negative pressure load on the liquid reservoir on the second surface side, and
   (B) an extracellular matrix-forming substance having cell fixing capability is attached on the circumference of the opening on the first surface side of a through hole on a substrate.

6. An electrode unit for planar patch clamp device, comprising the following constituents (a') to (c'):
   (a') a closed or sealed electrode vessel enclosed with a vessel wall, at least part of which is made of an inorganic porous material,
   (b') an electrode accommodated in the closed or sealed electrode vessel, noble metal chloride NmCl layer being formed on the surface of the noble metal Nm, and
   (c') an electrode solution filled in the closed or sealed electrode vessel, the noble metal chloride NmCl and an alkali metal chloride being dissolved therein at a saturated concentration,
   wherein the inorganic porous material of the vessel wall separates outside liquid from the electrode solution filled in the closed or sealed electrode vessel, and enables an electrical communication, but minimizes a fluid communication between the electrode solution and the outside liquid.

7. The electrode unit for planar patch clamp device according to claim 6, wherein the inorganic porous material composing at least part of the vessel wall is porous glass or porous ceramic.

8. The electrode unit for planar patch clamp device according to claim 6, wherein the noble metal Nm is silver Ag or platinum Pt, and the alkali metal chloride is potassium chloride KCl.

9. The electrode unit for planar patch clamp device according to claim 6, wherein the electrode is the following (C) or (D):
   (C) a stick electrode protruding inside the closed or sealed electrode vessel, the noble metal chloride NmCl layer being formed on the surface of a core made of the noble metal Nm, or
   (D) a cylindrical electrode formed on the inner periphery of the electrode vessel wall, wherein the bottom layer on the vessel wall side is a deposited layer of the noble metal Nm and the surface layer in contact with the electrode solution is a deposited layer of the noble metal chloride NmCl.

10. A cell ion channel current measurement method, which comprises
    introducing a conductive liquid into a liquid reservoir on the second surface side of the planar patch clamp device according to claim 1, and introducing a conductive liquid containing a cell to be measured dispersed therein into a liquid reservoir on the first surface side to conductively communicate between the liquid reservoir on the first surface side and the liquid reservoir on the second surface side;

disposing the cell at a prescribed position of the liquid reservoir on the first surface side;

applying a voltage between the electrodes of the electrode units on the first surface side and the second surface side; and measuring an ion channel current of the cell to be measured.

11. The cell ion channel current measurement method according to claim 10, wherein a plurality of liquid reservoirs are disposed on the first surface side of the substrate in the planar patch clamp device, a recess having a width larger than that of a cell body of a nerve cell and having a depth that can inhibit the movement of a cultured cell body is formed in these liquid reservoirs, a cell to be measured is a nerve cell, and a conductive liquid is a cell culture medium of the nerve cell.

12. The cell ion channel current measurement method according to claim 11, wherein a Ca probe for Ca imaging is introduced into a nerve cell in advance, and an ion channel current of the cell is measured by means at least including Ca imaging, which is observation of fluorescence that occurs at generation of cell action potential or at propagation of an action potential.

13. The cell ion channel current measurement method according to claim 12, wherein plural or many nerve cells into which a Ca probe is introduced are disposed on the first surface side in the planar patch clamp device, and synapses of these nerve cells mutually linked are defined as a nerve cell network, and a current is injected or a voltage is applied to a single nerve cell of these cells to perform measurement by the Ca imaging in the plural or many nerve cells.

* * * * *